United States Patent [19]

Kannankeril

[11] Patent Number: 4,925,453
[45] Date of Patent: May 15, 1990

[54] ABSORBENT BLOOD WIPE PAD AND METHOD

[75] Inventor: Charles P. Kannankeril, North Caldwell, N.J.

[73] Assignee: Sealed Air Corporation, Saddle Brook, N.J.

[21] Appl. No.: 230,575

[22] Filed: Aug. 10, 1988

[51] Int. Cl.$^5$ ............................................. A61F 13/00
[52] U.S. Cl. ................................. 604/378; 604/370; 604/385.1; 128/917; 15/104.94
[58] Field of Search ............ 604/358, 378, 381, 374, 604/289, 370, 385.1, 386, 392, 393; 128/849, 851, 888, 155, 917; 401/266; 15/104.94; 132/293, 294

[56] References Cited

U.S. PATENT DOCUMENTS

| | | | |
|---|---|---|---|
| 3,446,208 | 5/1969 | Fukuda | 128/156 |
| 3,521,624 | 7/1970 | Gander et al. | 128/849 |
| 3,661,680 | 5/1972 | Gore | 604/358 X |
| 3,737,939 | 6/1973 | Jones, Sr. | 15/104.94 X |
| 3,775,014 | 11/1973 | Rosborne | 15/104.94 X |
| 3,888,248 | 6/1975 | Moore et al. | 128/156 |
| 3,911,922 | 10/1975 | Kliger | 604/370 X |
| 3,989,867 | 11/1976 | Sisson | 128/156 X |
| 4,321,997 | 3/1982 | Miller | 206/204 |
| 4,382,507 | 5/1983 | Miller | 206/204 |
| 4,410,578 | 10/1983 | Miller | 428/117 |
| 4,417,894 | 11/1983 | Norris | 604/358 X |
| 4,519,798 | 5/1985 | Dinius | 604/358 |
| 4,540,414 | 9/1985 | Wishman | 604/378 |
| 4,575,891 | 3/1986 | Valente | 604/289 X |
| 4,617,021 | 10/1986 | Leuprecht | 604/365 |
| 4,704,107 | 11/1987 | Coates | 128/155 X |
| 4,773,408 | 9/1988 | Cilento et al. | 604/358 X |
| 4,780,352 | 10/1988 | Palumbo | 604/367 X |
| 4,798,603 | 1/1989 | Meyer et al. | 604/379 X |
| 4,813,944 | 3/1989 | Haney et al. | 604/358 |

FOREIGN PATENT DOCUMENTS 276863 11/1951 Switzerland ................. 132/293

Primary Examiner—Robert A. Hafer
Assistant Examiner—Kevin G. Rooney
Attorney, Agent, or Firm—Bell, Seltzer, Park & Gibson

[57] ABSTRACT

This invention relates to a medical sponge for use by medical personnel to wipe wounds, incisions and the like to absorb body fluids, such as blood, while protecting the person using the sponge from contact. The medical sponge comprises an absorbent pad enclosed which is covered on one face by fluid permeable cover sheet and on the other face by a fluid impervious cover sheet to enclose the absorbent pad. A handle is provided on the fluid impervious cover sheet for grasping and using the sponge while protecting the user from contact with blood absorbed in the absorbent pad.

21 Claims, 4 Drawing Sheets

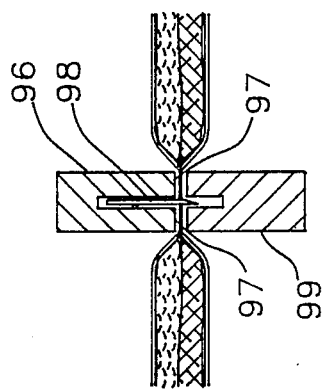
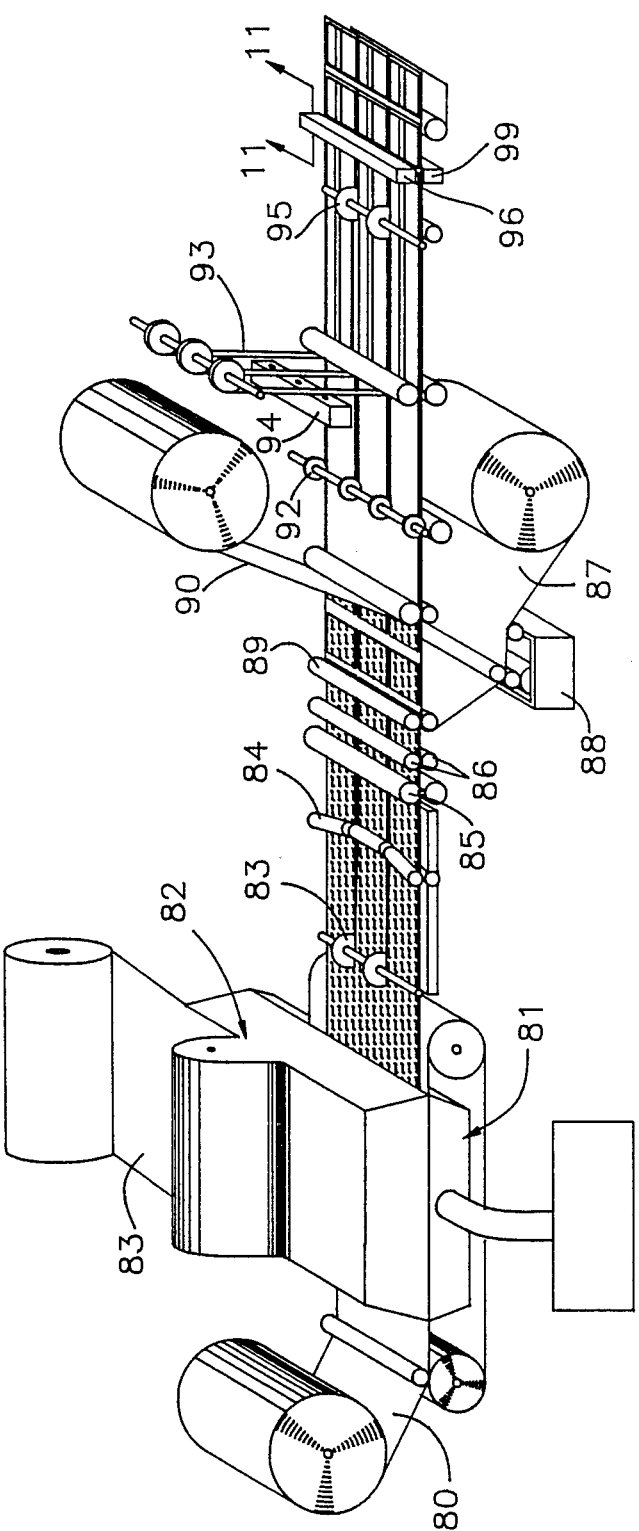

ABSORBENT BLOOD WIPE PAD AND METHOD

BACKGROUND OF THE INVENTION

This invention relates to a medical sponge for use by medical personnel to wipe wounds, incisions and the like to absorb body fluids, such as blood, while protecting the person using the sponge from contact with such body fluids.

FIELD OF THE INVENTION

It is conventional practice to wipe blood or other body fluids from incisions or wounds while providing medical treatment for a patient. Medical sponges, in the form of gauze pads have been used for many years for such purposes. Such gauze pads have typically comprised multiple layers of absorbent woven gauze or fabric secured together to form a pad of rectangular or square shape. The increasing prevalence of carriers of the AIDS virus has made using such conventional medical sponges potentially risky for the health provider. The AIDS virus is known to be present in blood and other body fluids of an infected person or carrier, so any contact with a carrier's body fluids presents a risk of contagion. Unfortunately, there is no effective way to readily identify carriers of the AIDS virus so it is becoming commonplace to treat virtually all persons as potential carriers of the AIDS virus.

Persons that treat wounds and incisions are currently taking precautions against exposure to the AIDS virus by using rubber gloves or other protective gear and avoiding the direct handling of all materials that come into contact with the blood or other body fluids wherever practical. For example, some people are using retractors or forceps to handle the conventional sponges so as not to directly handle or contact the blood soaked sponges. These are stop gap measures and are awkward. Additionally, use of such devices present sterilization problems and increase the cost of health care. There is a need for an effective device for absorbing blood that provides an increased measure of safety for health care personnel.

Accordingly, it is an object of the present invention to provide an absorbent pad for use by medical personnel to absorb body fluids and to protect the person using the pad from contact with such fluids. It is another object of the present invention to provide a method of making such pads in substantial quantities and at low cost.

SUMMARY OF THE INVENTION

The above and other objects are achieved by the present invention by a medical sponge which comprises a pad of absorbent material for absorbing body fluids therein. The pad has opposite faces and peripheral side edges and includes a fluid permeable cover sheet of non-absorbent material covering one of the faces, and a fluid impervious cover sheet of nonabsorbent, moisture impervious material covering at least the other face of the absorbent pad. At least one of the cover sheets covers the edges of the pad and extends into contiguous relation to the other cover sheet where the cover sheets are secured together to enclose the absorbent pad. A handle is attached to the fluid impervious cover sheet to provide an easy means of grasping and using the sponge. The present invention also provides a method of making the aforementioned medical sponge by forming the absorbent pad, covering one face thereof with the fluid permeable cover sheet, covering the other face thereof with the fluid impervious cover sheet, attaching the cover sheets together around the periphery of the pad and providing handle means on the outside of the fluid impervious cover sheet for ease in handling and use of the sponge without contact with body fluids.

BRIEF DESCRIPTION OF THE DRAWINGS

Some of the objects having been stated, other objects will appear as the description proceeds, when taken in connection with the accompanying drawings in which

FIG. 10 is a schematic diagram of an apparatus and method for commercially fabricating an absorbent pad embodying the features of the present invention; and FIG. 11 is an enlarged sectional view taken substantially along the line 11—11 of FIG. 10.

DETAILED DESCRIPTION OF THE PREFERRED EMBODIMENT

Figure 1:
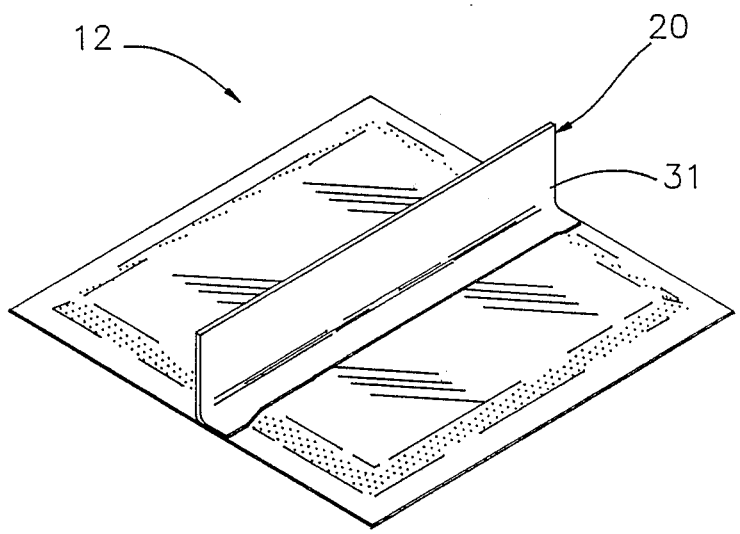
FIG. 1 is a perspective view of a medical sponge embodying the features of the present invention.

Referring more particularly to the drawings, FIGS. 1–4 illustrate one embodiment of a medical sponge 12 incorporating the features of the present invention and provides a useful absorbent device for use by medical personnel. The sponge 12 is generally rectangular in shape and comprises a pad 14 of liquid absorbent material, a fluid permeable cover sheet 16 covering one face of the pad, a fluid impervious cover sheet 18 covering at least the other face of the pad, and handle means 20 attached to the outer surface of the fluid impervious cover sheet 18.

Figure 2:
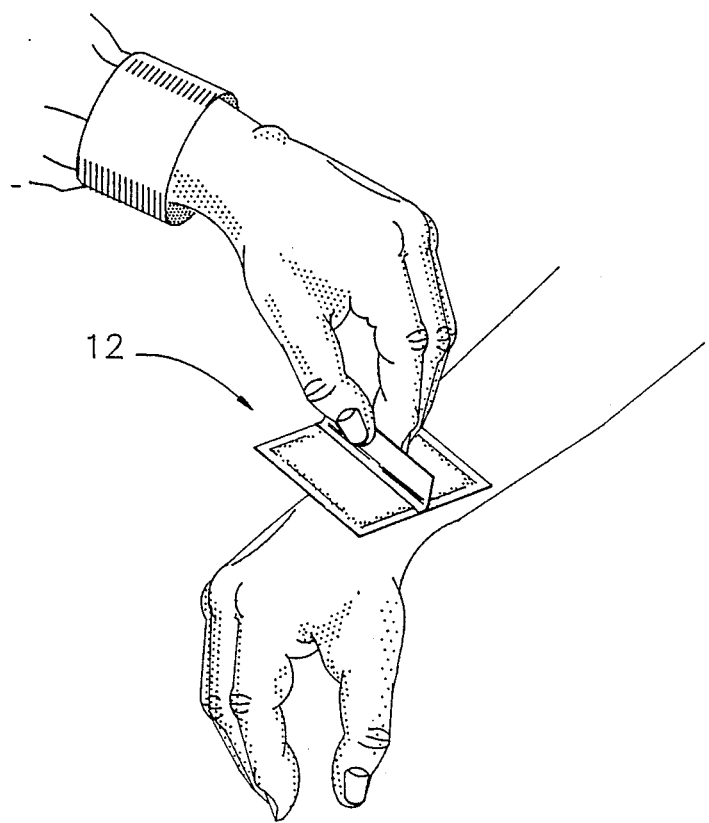
FIG. 2 is a perspective view of the medical sponge as it is held by the hand of a user during use.
Figure 3:
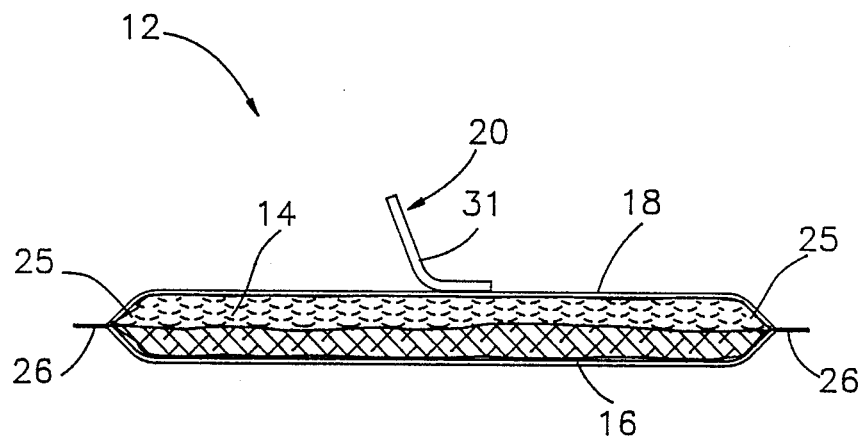
FIG. 3 is an enlarged sectional view of the medical sponge taken substantially along the line 4—4 of FIG. 1.

In use, as best seen in FIG. 2, the medical sponge 12 is held by the handle means 20 and used, for example, to wipe an abrasion or cut on the hand of a patient. Note that by holding the sponge 12 by the handle 20, the fingers and thumb of the user are shielded behind the sponge from contact with the local area of the patient that is bleeding. Also, there is no compression of the pad 14 so that it may fully absorb and retain the fluids within the enclosed absorbent pad.

The pad 14 of liquid absorbent material is made of hydrophilic materials such as conventional defiberized wood pulp (also known as wood fluff), synthetic pulp, such as rayon, or cotton. The thickness of the pad 14 may be varied as desired depending upon the amount of absorbency required and is typically between 1/16 to ½ inch thick. In a preferred embodiment as illustrated herein, the pad 14 comprises a layer of tissue-like paper wadding 23 and a layer of wood fluff 24. The layer of wood fluff 24 is formed into a compressed batt in the manner of a non-woven fabric, and as further described below. The paper wadding 23 may be produced in any conventional manner, such as on a Fourdrinier paper machine, and may, if desired, be creped for added body. The wadding typically has a texture similar to household facial tissue and has substantially more integrity than does the wood fluff. The multiple layer absorbent pad 14 has the capacity to absorb and retain many times its weight in liquid.

The fluid permeable cover sheet 16 is arranged to cover the bottom face of the absorbent pad 14 so as to contact the body fluid. In that regard, the fluid permeable cover sheet 16 must allow easy penetration of liquid without harming or irritating the patient and, preferably, without absorbing the body fluid itself. In the preferred embodiment, the fluid permeable cover sheet 16 is a hydrophobic non-woven material composed of polypropylene filaments and is particularly characterized by the ability to wick liquid through the material without absorbing any of the liquid. The non-woven polypropylene material particularly features the ability to wick the liquid through while maintaining a dry feel. It is also smooth and soft and poses no known risks to the patient. Such a non-woven material is commercially available from a number of sources.

The fluid impervious cover sheet 18 covers the top face of the absorbent pad 14 and forms an effective barrier between the person using the sponge and any body fluids of the patient. In that regard, the fluid impervious cover sheet 18 must be nonabsorbent and impervious to any liquid. In the preferred embodiment, the fluid permeable cover sheet 18 is formed of a polyolefin film, such as polyethylene.

Figure 4:
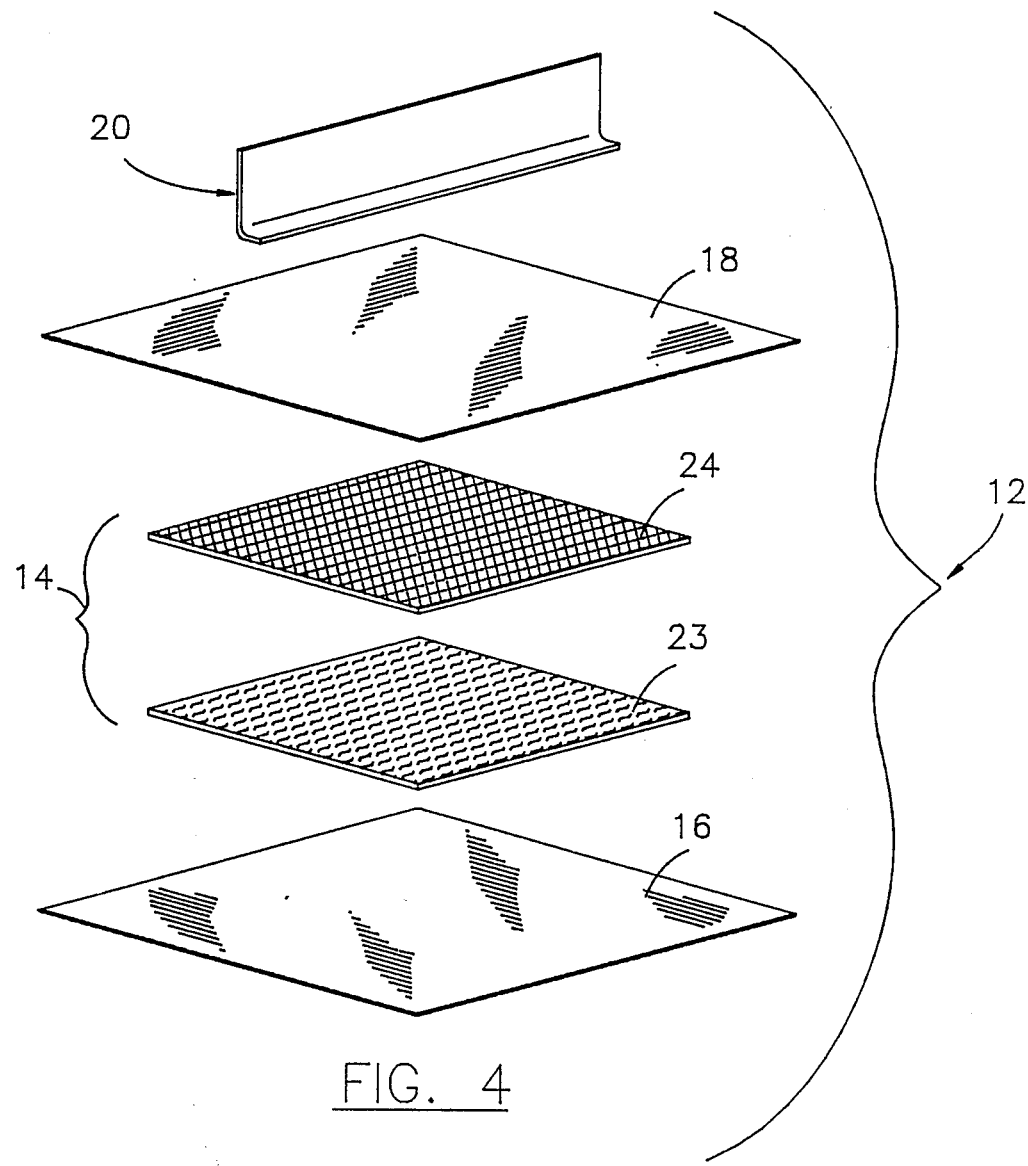
FIG. 4 is an exploded perspective view of the medical sponge shown in FIG. 1.

As best illustrated in FIG. 4, the cover sheets 16 and 18 cover the peripheral side edges 25 of the pad and extend into a contiguous relation are secured together around their periphery. The absorbent pad 14 is thereby enclosed between the cover sheets 16 and 18. The edges of the cover sheets are secured together as shown at 26 by any suitable means, such as heat sealing or hot melt adhesive. Sealing the edges of the cover sheets maintains the absorbent pad 14 and any fluids absorbed therein within the cover sheets 16 and 18 and prevents migration of such fluids to the outside surface which is an important safety and protection feature of the instant medical sponge.

The handle means 20 is positioned on the outside surface of the fluid impervious cover sheet 18 so that the hand of a person using the sponge is effectively shielded from contact with the patient, or, more particularly, the wound of the patient and the body fluid. The handle means 20 includes a grasping portion which is generally medially disposed on the outer face of the fluid impervious cover sheet 18 and extending generally outwardly therefrom. The grasping portion is thus isolated from the pad of absorbent material by the fluid impervious cover sheet. This makes more effective use of the fluid impervious cover sheet by effectively putting the fingers and thumb of the user centrally behind the impervious sheet. Additionally, handle means 20 permits the sponge to be handled without impeding the absorbency thereof or squeezing absorbed fluid out of the pad.

The handle means 20 may take many different forms, some of which are as shown in FIGS. 1 and 5-9. In FIG. 1, the handle means 20 is formed of an elongate strip 31 that is adhesively secured along one longitudinal edge. Any suitable material may be used as the strip 31, such as paper or polyolefin film. The remaining unsecured portion of the strip 31 forms a handle and the medial portion of which defines the grasping portion which may be grasped as shown in FIG. 2.

Figures 5, 6:
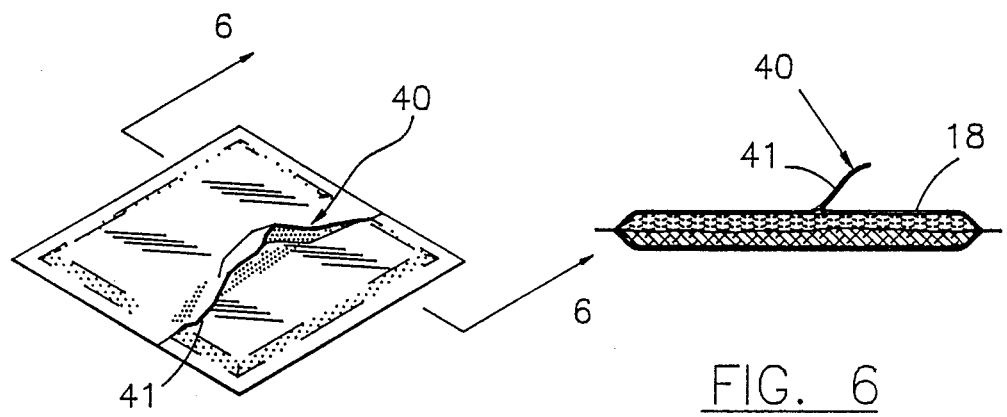
FIG. 5 is a perspective view a medical sponge similar to FIG. 1, but illustrating a second embodiment of the handle means.
FIG. 6 is a sectional view of the medical sponge shown in FIG. 5, taken substantially along line 6—6 of FIG. 5.

In FIGS. 5 and 6, a second embodiment of the present invention is illustrated, in which the sponge is the same as that described above, except that a handle means 40 is formed integral with the fluid impervious cover sheet 18. The cover sheet 18 is folded longitudinally to form a gusset or pleat 41 defining a folded flap portion by which the sponge may be grasped. The ends of the fold 41 are secured with the edges of the cover sheets 16 and 18 so that the fold lies flat when not in use.

Figures 7, 8:
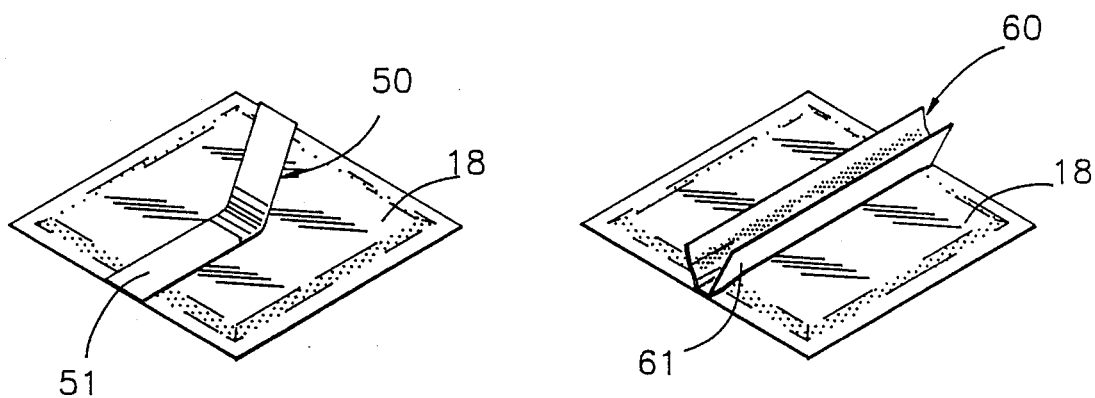
FIG. 7 is a perspective view of a medical sponge similar to FIG. 1, but illustrating a third embodiment of the handle means.
FIG. 8 is a perspective view of a medical sponge similar to FIG. 1, but illustrating a fourth embodiment of the handle means.

In FIG. 7, a third embodiment of the sponge of the present invention is illustrated and which differs from the previously described sponges only in that handle means 50 is formed of an elongate strip 51, similar to strip 31, except that it is adhesively attached to cover sheet 18 at one end rather than along one edge. The other end of the strip 51 forms a free end defining the grasping portion by which the sponge may be grasped.

In FIG. 8, a fourth embodiment is illustrated, in which handle means 60 is formed of an elongate strip 61, similar to strips 31 and 51, except that it is adhesively secured to cover sheet 18 along a longitudinally extending center portion. The remaining, unsecured longitudinal edges of the strip 61 form free flaps defining the grasping portion by which the sponge may be easily grasped.

Figure 9:
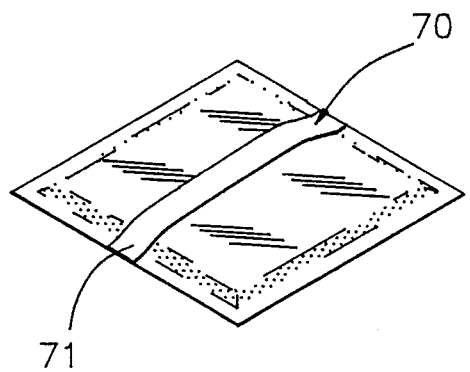
FIG. 9 is a perspective view of a medical sponge, but illustrating a fifth embodiment of the handle means.

In FIG. 9, a fifth embodiment is illustrated in which handle means 70 is formed of an elongate strip 71, similar to strips 31, 51 and 61, except that it is adhesively secured to the fluid impervious cover sheet at opposite end portions of the strip 71. The unsecured middle portion of strip 71 forms an open loop defining the grasping portion by which the sponge may be handled, but which that lays flat when not in use.

FIG. 10 schematically illustrates an apparatus and method for fabricating the medical sponge shown in FIGS. 1 and 7-9. As illustrated, a web of paper wadding 80 is withdrawn from a supply roll and advanced into and through a vacuum deposition apparatus 81. Positioned above the vacuum deposition apparatus 81 is a shredding apparatus 82 which shreds a web of absorbent material 83, which is also withdrawn from a supply roll, into a defiberized mass and deposits it on the advancing web of paper wadding 80. The vacuum deposition apparatus 81 draws the defiberized mass down onto the wadding 80 and forms a layer or batt of substantially uniform thickness. The paper wadding 80 and defiberized batt define layers of absorbent material which are further processed to form the absorbent pad 14.

These layers of absorbent material are slit by cutters 83 into longitudinal strips and these strips are separated by rollers 84. The strips are cut to length into individual pads by a transverse cutter 85. The individual pads 14 are advanced away from the strips by a pair of rollers 86 to form a space between successive rows of absorbent pads 14.

A web of permeable non-woven hydrophobic material 87 is withdrawn from a supply roll and delivered through an adhesive applicator 88 to a pair of rollers 89 which also deposit the absorbent pads 14 onto the web 87. The adhesive is preferably applied in a pattern which matches the land areas of the material between the pads.

A web of fluid impervious polyolefin film 90 is withdrawn from a supply roll and brought onto the advancing absorbent pads and non-woven material 87 by a pair of rollers 91. Rotating disks 92 press the longitudinal edges and longitudinal land areas of the non-woven web 87 and impervious web 90 together so that the adhesive secures such areas of the webs together with a good seal.

Three strips of handle material 93 are withdrawn from supply rolls and brought through an adhesive applicator 94 and then onto the advancing polyolefin film 90 to form handle means on the outside surface of the film. The adhesive is applied in a desired pattern to securely attach the strip to the film while allowing a free portion to fold away from the film for easy handling of the sponge.

The components then pass through a slitter 95 which slits the secured together webs 87 and 90 longitudinally along the center of the land areas to separate the webs into three separate webs. These three webs then pass through a cutter 96 which presses the transverse land areas of webs 87 and 90 together so that the adhesive secures those areas of the webs 87 and 90 together and simultaneously cuts the three webs into individual sponges 12. The cutter 96 is illustrated in more detail in FIG. 11. Cutter 96 includes shoulders 97 on opposite sides of a cutting blade 98 and an anvil 99 which receives the cutting blade 98 in a groove therein.

In the case of an integrally formed handle as illustrated in FIGS. 5 and 6, the web of film 90 will be folded longitudinally by conventional folding means, not shown, to form a gusset or pleat therein. Alternatively, the web may be prefolded and supplied with the gusset or pleat already therein.

In the drawings and specification there has been set forth preferred embodiments of the invention, and although specific terms are employed, they are used in a generic and descriptive sense only and not for purposes of limitation.

That which is claimed:

1. A medical sponge characterized by the ability to absorb body fluids, such as blood, while protecting persons using the sponge from contact with such body fluids, said sponge comprising:
    (a) a pad of absorbent material for absorbing body fluids therein and having opposite faces and peripheral side edges;
    (b) a fluid permeable cover sheet of nonabsorbent material covering one face of said absorbent pad;
    (c) a fluid impervious cover sheet of flexible plastic film material covering at least the other face of said absorbent pad;
    (d) at least one of said cover sheets also covering said side edges of said pad and extending into contiguous relation to said other cover sheet;
    (e) said cover sheets being secured together where they are contiguous to enclose said absorbent pad therebetween; and
    (f) handle means on the face of said fluid impervious cover sheet opposite from said pad of absorbent material and having a medially disposed grasping portion extending generally outwardly therefrom for ease in grasping and using said sponge to wipe wounds, incisions and the like to absorb body fluids, said handle means grasping portion being isolated from said pad of absorbent material by said fluid impervious cover sheet to protect the person using the sponge from contact with such body fluids.

2. The medical sponge according to claim 1 wherein said fluid permeable cover sheet comprises a hydrophobic material characterized by the ability to allow a liquid to wick through the material without absorbing any of the liquid.

3. The medical sponge according to claim 1 wherein said fluid impervious cover sheet comprises a polyolefin film.

4. The medical sponge according to claim 1 wherein said pad of absorbent material comprises a plurality of layers of absorbent material.

5. The medical sponge according to claim 1 wherein said handle means comprises an elongate strip attached to said fluid impervious cover sheet along one longitudinal edge of said strip with the remainder thereof being unattached so that said remainder of said strip defines said grasping portion by which the sponge may be grasped and used.

6. The medical sponge according to claim 1 wherein said handle means is formed integral with said fluid impervious cover sheet.

7. The medical sponge according to claim 6 wherein said handle means comprises a folded flap formed in said fluid impervious cover sheet wherein said folded flap defines said grasping portion by which the sponge may be grasped and used.

8. The medical sponge according to claim 1 wherein said handle means comprises an elongate strip attached to said fluid impervious cover sheet at one end portion of said strip with the remainder of said strip being unattached so that the remainder of said strip defines said grasping portion by which the sponge may be grasped and used.

9. The medical sponge according to claim 1 wherein said handle means comprises an elongated strip attached to said fluid impervious cover sheet along a longitudinally extending center portion of said strip with the remainder thereof being unattached so that the remainder of said strip form free flaps defining said grasping portion by which the sponge may be grasped and used.

10. The medical sponge according to claim 1 wherein said handle means comprises an elongated strip attached to said fluid impervious cover sheet at opposite end portions of said strip with the medial portion thereof being unattached so that the medial portion of said strip forms a loop defining said grasping portion by which the sponge may be grasped and used.

11. A medical sponge characterized by the ability to absorb body fluids, such as blood, while protecting persons using the sponge from contact with such body fluids, said sponge comprising:
    (a) a pad of absorbent material for absorbing body fluids therein and having opposite faces and peripheral side edges;
    (b) a fluid permeable cover sheet of nonabsorbent material covering one face of said absorbent pad;
    (c) a fluid impervious cover sheet of flexible plastic film material covering at least the other face of said absorbent pad;
    (d) said cover sheets extending a predetermined distance beyond the peripheral side edges of said pad and into contiguous relation with each other;
    (e) said cover sheets being secured together along their contiguous peripheral edges beyond the peripheral edges of said absorbent pad to enclose said pad therebetween; and (f) handle means on the face of said fluid impervious cover sheet opposite from said pad of absorbent material and having a medially disposed grasping portion extending generally outwardly therefrom for ease in grasping and using said sponge to wipe wounds, incisions and the like to absorb body fluids, said handle means grasping portion being isolated from said pad of absorbent material by said fluid impervious cover sheet to protect the person using the sponge from contact with such body fluids.

12. The medical sponge according to claim 11 wherein said fluid permeable cover sheet comprises a non-woven polypropylene material.

13. The medical sponge according to claim 11 wherein said fluid impervious cover sheet comprises polyethylene film.

14. The medical sponge according to claim 11 wherein said absorbent pad comprises a layer of paper wadding and a layer of defiberized wood pulp.

15. A method of manufacturing a disposable medical sponge having the ability to absorb body fluids, such as blood, while protecting persons using the sponge from contact with such body fluids, said method comprising the steps of:

(a) forming a pad of absorbent material having opposite faces and peripheral side edges;

(b) covering a first face of said absorbent pad with a fluid permeable cover sheet;

(c) covering the other face of said absorbent pad with a fluid impervious cover sheet of flexible plastic film;

(d) extending at least one of said cover sheets to cover the peripheral side edges of said pad and into contiguous relation with the other cover sheet;

(e) securing said cover sheets to one another where they are contiguous to enclose said absorbent pad; and (f) providing handle means on the face of said fluid impervious cover sheet opposite from said pad of absorbent material so as to have a medially disposed grasping portion extending generally outwardly therefrom for ease in grasping and using the sponge to wipe wounds, incisions and the like to absorb body fluids such that the handle means grasping portion is isolated from the pad of absorbent material by the fluid impervious cover sheet to protect the person using the sponge from contact with such body fluids.

16. The method according to claim 15 wherein said step of providing handle means on said fluid impervious cover sheet comprises forming a handle integral with said fluid impervious cover sheet.

17. The method according to claim 16 wherein the step of forming the handle integral with said impervious cover sheet comprises folding said impervious cover sheet to form a gusset defining the grasping portion, and securing the ends of the gusset where the cover sheets are contiguous and secured together.

18. The method according to claim 15 wherein said step of covering the faces of the absorbent pad includes extending said cover sheets a predetermined distance beyond said peripheral side edges of said absorbent pad and said step of securing said cover sheets comprises securing said cover sheets together along their peripheral edges beyond the peripheral side edges of said absorbent pad.

19. The method according to claim 15 wherein said step of providing handle means on said fluid impervious cover sheet comprises attaching an elongate strip at one end portion of said strip while leaving the remainder thereof unattached so as to define the grasping portion by which the sponge may be grasped and used.

20. The method according to claim 15 wherein said step of providing handle means on said fluid impervious cover sheet comprises attaching an elongate strip along a longitudinally extending center portion of said strip while leaving the remainder thereof unattached so that the remainder of said strip form free flaps to define the grasping portion by which the sponge may be grasped and used.

21. The method according to claim 15 wherein said step of providing handle means on said fluid impervious cover sheet comprises attaching an elongate strip at opposite end portions of said strip while leaving the medial portion thereof unattached so that the mid portion of said strip forms a loop defining the grasping portion by which the sponge may be grasped and used.

* * * * *